United States Patent [19]

Wehrli

[11] Patent Number: 5,410,056
[45] Date of Patent: Apr. 25, 1995

[54] METHOD FOR THE PRODUCTION OF FOLIC ACID

[75] Inventor: Christof Wehrli, Witterswil, Switzerland

[73] Assignee: Hoffman-La Roche Inc., Nutley, N.J.

[21] Appl. No.: 178,195

[22] Filed: Jan. 6, 1994

[30] Foreign Application Priority Data

Jan. 26, 1993 [CH] Switzerland .................... 214/93

[51] Int. Cl.$^6$ ............................................ C07D 475/04
[52] U.S. Cl. ................................. 544/261; 558/190; 560/35; 562/440; 568/494
[58] Field of Search ................ 562/440; 560/35; 558/190; 544/261

[56] References Cited

U.S. PATENT DOCUMENTS 5,334,957  9/1994  Bouy .................... 562/440

OTHER PUBLICATIONS

Angier, et al. (JACS, 70) (1948), 25) Synthesis of Pteroylglutamic Acid. III.
Eistert, et al. (Chem. Ber 88 (1955), 939, Investigations with triose reductone.
Abstract of the Eistert publication: Investigations with triose reductone (1955).

*Primary Examiner*—Ronald G. Daus
*Attorney, Agent, or Firm*—George M. Gould; William H. Epstein; Catherine A. Picut

[57] ABSTRACT

The present invention is directed to a novel process for the production of folic acid in high yield utilizing a novel diimine as an intermediate. This diimine is formed by reacting 2-substituted malondialdehyde with p-aminobenzoyl-L-glutamic acid. This diimine may be converted into folic acid by reacting said diimine with triaminopyrimidinone in the presence of sulphite.

10 Claims, No Drawings

METHOD FOR THE PRODUCTION OF FOLIC ACID

BACKGROUND OF THE INVENTION

Methods for producing folic acid have been described. Robert B. Angier et al. (JACS, 70 (1948), 25) describe the manufacture of folic acid using halogen-free compounds by reacting p-aminobenzoyl-L-glutamic acid diethyl ester with 2-hydroxymalondialdehyde, isolating p-(2,3-dihydroxy-2-ene-propylideneamino)-benzoic acid diethyl ester and reacting the intermediate with triaminopyrimidinone. In this synthesis, in which an imine is isolated as the intermediate, folic acid is obtained in only 12.6% yield.

Other methods for producing folic acid are described in O. Isler, G Brubacher, S. Ghisla, B. Kräutler, Vitamine II; G. Thieme Verlag Stuttgart; (1988).

These methods for producing folic acid described to date have the common disadvantage of resulting in a low yield of folic acid.

The object of the present invention is to provide a process for the production of folic acid in substantially higher yield (up to 84%) compared with known processes, by using a novel diimine as an intermediate.

The production of diimines has been described. B. Eistert et al. (Chem. Ber., 88 (1955), 939) describe the production of diimines by reacting 2-hydroxy malondialdehyde with aromatic amines such as aniline, p-aminobenzoic acid or p-amino benzoic acid ester.

SUMMARY OF THE INVENTION

The present invention is directed to a novel process for producing folic acid by utilizing as an intermediate a novel diimine of formula I,

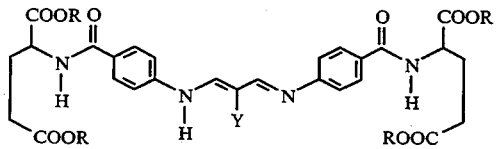

wherein R is hydrogen or lower alkyl and Y is hydroxy, halogen, phosphate, diphosphate, triphosphate or —O—COR' and R' is lower alkyl or phenyl.

The diimines of formula I are novel compounds and are also an object of the invention. By utilizing said diimine as an intermediate in the production of folic acid, in accordance with this invention, folic acid may be produced in a substantially higher yield than other known methods for producing folic acid and largely without formation of byproducts.

DETAILED DESCRIPTION OF THE INVENTION

The present invention is directed to a novel process for producing folic acid by utilizing as an intermediate a novel diimine of formula I,

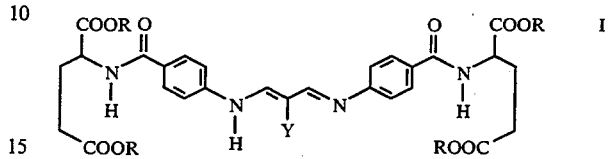

wherein R is hydrogen or lower alkyl and Y is hydroxy, halogen, phosphate, diphosphate, triphosphate or —O—COR' in which R' is lower alkyl or phenyl.

The diimines of formula I above are novel compounds and are also an object of the invention.

This diimine is formed by reacting 2-substituted malondialdehyde with p-aminobenzoyl-L-glutamic acid. Said diimine may be converted into folic acid by reacting said diimine with triaminopyrimidine in the presence of sulphite at a pH value of 3 to 8.

As used throughout this specification, the term "lower alkyl" signifies straight-chain or branched alkyl groups with 1 to 6 carbon atoms such as methyl, ethyl, propyl, iso-propyl, butyl, iso-butyl, tert-butyl, pentyl, hexyl and the like. Of the straight-chain alkyl groups, methyl and ethyl are preferred. As used throughout this specification, "phosphate" refers to any conventional monophosphate.

The "halogen" may be any halogen such as chlorine, bromine or iodine. Bromine is the preferred halogen.

The preferred diimine of formula I is where R is hydrogen and Y is hydroxy.

The process to produce folic acid from such novel diimines comprises reacting a diimine of formula I above with triaminopyrimidinone in an aqueous medium in the presence of sulphite, or inorganic compounds which form sulphites in water, at a pH value of 3–8 and temperatures of about 0°–100° C. The sulphite may be added to the aqueous medium, or alternatively may be formed in situ by the addition of inorganic compounds, which form sulphites in water, to the aqueous medium. Any inorganic compound which forms sulphites in water may be used, such as $Na_2SO_3$, $K_2SO_3$, $NaHSO_3$, $Na_2S_2O_5$ or $SO_2$ and the like. The use of triaminopyrimidinone sulphite is also possible.

The conversion of the diimines of formula I into folic acid or folic acid alkyl esters of formula II takes place according to the following Reaction Scheme:

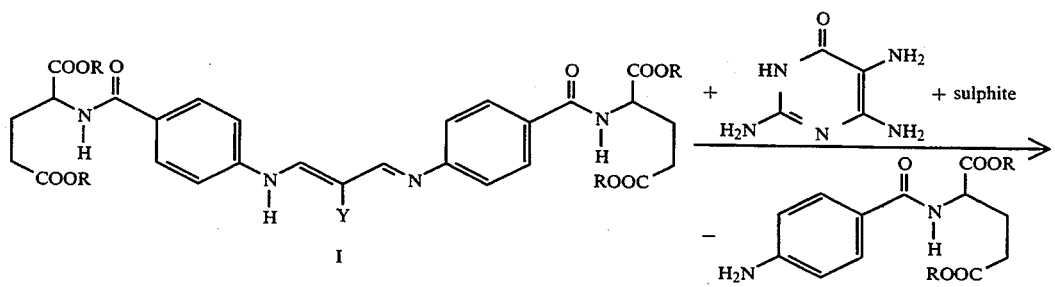

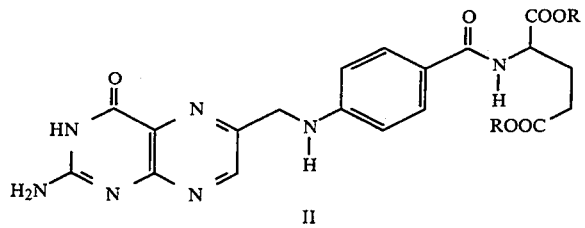

II

The aforementioned sulphites used in the conversion of diimines of formula I into folic acid or the folic acid alkyl esters of formula II are essential to avoid the formation of byproducts. Without these sulphites, the formation of byproducts is favoured.

Preferably, at least about one mol equivalent of triaminopyrimidinone is reacted with a mol equivalent of diimine of formula in the presence of 0.3–3 mol equivalents of sodium sulphite per mol equivalent of diimine at a pH value of 5–7 and a temperature in the range of 5° C. to 40° C. Best results are obtained when 1 mol equivalent of sodium sulphite is used per mol equivalent of diimine and the reaction is carried out at about 10° C. The conversion of a compound of formula I to formula II can be effected in aqueous solution or also in water-miscible, inert, organic solvents. Water is the preferred solvent. When water-miscible, inert, organic solvents are used acetonitrile, dimethylformamide, dioxan, methanol, tetrahydrofuran and the like may be used. Where such organic solvents are used, these solvents should be mixed with water and the water content should be greater than 30%. Furthermore, the reaction of triaminopyrimidone with diimine of formula I is conveniently effected at a concentration of reactants of about 0.05–1 mol per liter of aqueous solution or solvent. Best results are obtained when the concentration of reactants is preferably 0.1–0.5 mol per liter of such solution or solvent.

The diimines of formula I which are used as starting materials in the process of manufacturing folic acid can be prepared in a manner known per se, e.g. by reacting 2-substituted malondialdehydes of formula III,

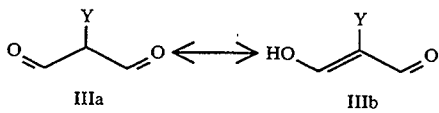

wherein Y is as above in formula I, with p-aminobenzoyl-L-glutamic acid or a p-aminobenzoyl-L-glutamic acid ester of formula IV,

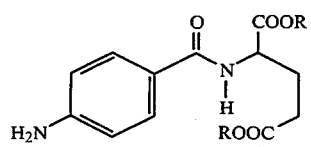

wherein R is as above in formula I, in an aqueous medium while said aqueous medium is under acidic conditions. At least about two (2) mol equivalents of p-aminobenzoyl-L-glutamic acid or p-aminobenzoyl-L-glutamic acid ester of formula IV can be used per mol equivalent of 2-substituted malondialdehyde of formula III. The reaction can be effected in an aqueous medium, with or without the addition of inert, water-miscible, organic solvents. These organic solvents may be any of the organic solvents described above.

Best results are obtained when 2-hydroxymalondialdehyde is reacted with p-aminobenzoyl-L-glutamic acid at pH values less than 4 and in a temperature range from about 0° C. to about 60° C.

The diimines of formula I can also be prepared by the process of reacting 2-substituted malondialdehyde tetraalkyl acetal or 2-substituted malondialdehyde dialkyl hemiacetal of formula V,

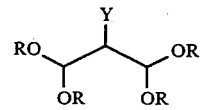

wherein R and Y are as above, with p-aminobenzoyl-L-glutamic acid or p-aminobenzoyl-L-glutamic acid ester of formula IV, described above, in acid hydrolysis conditions. Under acidic hydrolysis conditions the compounds of formula V yield in situ 2-substituted malondialdehydes of formula III from which the diimines of formula I can then be formed by the reaction described above.

Acid hydrolysis of a compound of formula V may be performed by any conventional acid hydrolysis means.

It is preferred to perform said acid hydrolysis in the presence of an ion-exchanger. Said acid hydrolysis to convert compounds of formula V to compounds of formula III is novel when performed in the presence of a ion-exchanger. The preferred ion-exchanger for this reaction is DOWEX 50W.

The diimines of formula I which are used as starting materials in the production of folic acid in accordance with this invention can be isolated after their preparation by known means. However, these diimines can also be prepared in situ and the manufacturing of folic acid can accordingly be carried out in a one-pot process by simultaneously reacting a compound of formula III, a compound of formula IV and triaminopyrimidinone in aqueous medium in the pressence of a sulphite, as described above. This one-pot process may or may not involve the addition of inert, organic solvents described above.

When diimines of formula I, in which R is lower alkyl, are used as starting materials, then there are obtained folic acid alkyl esters. Said esters can be hydrolyzed in a known manner before the folic acid is isolated.

After separation of the folic acid from the filtrate by known means, p-aminobenzoyl-L-glutamic acid can be extracted with a suitable solvent such as butanol, methyl acetate and the like or with a mixture of such solvents. In this manner, the p-aminobenzoyl-L-glutamic acid may be recycled.

Yields of folic acid of up to about 84% of theory can be achieved using the process in accordance with the invention.

The following Examples show especially advantageous embodiments of the process in accordance with the invention and are not in any way intended to be a limitation.

EXAMPLE 1

Preparation of
(S)-2-[4-[3-[4-[(S)-1,3-Dicarboxy-propylcarbamoyl]-phenylimino]-2-hydroxy-propenylamino]benzoylamino]-pentane-1,5-di-acid as the Diimine of Formula I and Conversion of the Diimine into Folic Acid 3.6 g (20 mmol) of 1,1,3,3-tetramethoxy-2-propanol and 40 ml of 1N HCl are placed in a 100 ml 5-necked flask provided with a thermometer and a stirrer under nitrogen and the mixture is stirred at 50° C. for 5 minutes. Thereafter, 10.65 g (40 mmol) of p-aminobenzoyl-L-glutamic acid are added and the mixture is stirred at 50° C. for 1 hour. After the addition of about 200 ml of water the diimine is left to crystallize at room temperature for 24 hours, filtered off and the filtered-off precipitate is washed with water. After drying under a water-jet vacuum at 60° C. there are obtained 10.1 g of (S)-2-[4-[3-[4-[(S)-1,3-dicarboxypropylcarbamoyl]-phenylimino]-2-hydroxy-propenylamino]benzoylamino]-pentane-1,5-di-acid with a water content of 4%. Yield=83% of theory; m.p.=172°–178° C.

20 ml of water and 2.52 g of sodium sulphite are added to 6.1 g of (S)-2-[4-[3-[4-[(S)-1,3-dicarboxypropylcarbamoyl]-phenylimino]-2-hydroxy-propenylamino]benzoylamino]-pentane-1,5-di-acid with a water content of 4% under nitrogen. The mixture is adjusted to a pH value of 6.0 with 2M sodium carbonate solution while stirring. 2.39 g (10 mmol) of triaminopyrimidinone sulphate are added to the suspension at room temperature while stirring slowly. The pH value is held constant at pH=6.0 by dosing with 2M sodium carbonate solution. The reaction has finished after 4 hours. The folic acid is determined in the red-brown mixture. For this purpose, the reaction mixture is diluted to exactly 250 ml with about 220 ml of water and an aliquot is removed therefrom in order to determine the folic acid yield using HPLC (high pressure liquid chromatography). Yield of folic acid=69% of theory based on diimine used.

EXAMPLE 2

Production of Folic Acid by Reacting p-Aminobenzoyl-L-glutamic Acid, 2-Hydroxymalondialdehyde and Triaminopyrimidinone in Aqueous Medium (One-Pot Process)

5.32 g (20 mmol) of p-aminobenzoyl-L-glutamic acid and 20 ml (2 mmol) of 0.1N HCl are placed under nitrogen in a 100 ml 5-necked flask provided with a thermometer and stirrer. 0.88 g (10 mmol) of 2-hydroxymalondialdehyde are added thereto and rinsed in with 3 ml of water. The suspension is stirred at room temperature for 1 hour. Thereafter, 4.25 ml of 2M sodium carbonate solution are added and the mixture is stirred for about 20 minutes. Thereafter, 2.52 g (20 mmol) of sodium sulphite are added and the mixture is warmed to 38° C. 2.39 g (10 mmol) of triaminopyrimidinone sulphate are added portionwise to the suspension in the course of 1 hour while stirring at pH=6.0. The pH value is held constant at pH=6.0 by dosing with about 7.6 ml of 2M sodium carbonate solution. The reaction has finished after 4 hours. The folic acid is determined in the red-brown mixture as described in Example 1. Yield of folic acid=68% of theory based on 2-hydroxymalondialdehyde used.

For the isolation of the folic acid from this solution the pH value is adjusted to 3.0 with acetic acid. The folic acid precipitates and can be filtered off. There are obtained 3.08 g of folic acid crude product having a content of 91% of pure L-folic acid=63.5% of theory.

The unreacted p-aminobenzoyl-L-glutamic acid is recovered from the filtrate by exhaustively extracting with methyl acetate at pH=3.0. There are obtained 3.23 g of p-aminobenzoyl-L-glutamic acid crude product having a content of 90% of pure p-aminobenzoyl-L-glutamic acid. The content of pure p-aminobenzoyl-L-glutamic acid is determined by HPLC.

EXAMPLE 3

Production of Folic Acid by Reacting p-Aminobenzoyl-L-glutamic Acid, 2-Hydroxymalondialdehyde and Triaminopyrimidinone in Aqueous Medium with the Addition of Organic Solvents 5.32 g (20 mmol) of p-aminobenzoyl-L-glutamic acid, 12.5 ml of 0.2N HCl, 12.5 ml of acetonitrile and 0.88 g (10 mmol) of 2-hydroxymalondialdehyde are mixed well under nitrogen in a 100 ml 5-necked flask provided with a thermometer and stirrer and the mixture is left to stand at room temperature for 24 hours. Thereafter, 2.52 g (20 mmol) of sodium sulphite are added and the mixture is warmed to 38° C. 2.39 g (10 mmol) of triaminopyrimidinone sulphate are slowly added to this mixture while stirring at pH=6.0. The pH value is held constant at pH=6.0 by dosing with 2M sodium carbonate solution. The reaction has finished after six hours. The folic acid in the red-brown mixture is determined at described in Example 1. HPLC analysis gives a folic acid yield of 73% of theory.

EXAMPLE 4

Production of Folic Acid by Reacting p-Aminobenzoyl-L-glutamic Acid, 2-Hydroxymalondialdehyde and Triaminopyrimidinone in Aqueous Medium with the Addition of Organic Solvents 5.32 g (20 mmol) of p-aminobenzoyl-L-glutamic acid, 12.5 ml of 0.2N HCl, 12.5 ml of acetonitrile and 0.88 g (10 mmol) of 2-hydroxymalondialdehyde are mixed well under nitrogen in a 100 ml 5-necked flask provided with a thermometer and stirrer and the mixture is left to stand at room temperature for 24 hours. Thereafter, 1,26 g (10 mmol) of sodium sulphite and 9 ml of 2M Sodium carbonate solution are added and the mixture is stirred for one hour at 10° C. 2.39 g (10 mmol) of triaminopyrimidinone sulphate are slowly added to this mixture at 10° C. while stirring at pH=6.0. The pH value is held constant at pH=6.0 by dosing with 2M sodium carbonate solution. The reaction has finished after six hours. The folic acid in the red-brown mixture is determined at described in Example 1. HPLC analysis gives a folic acid yield of 84% of theory.

EXAMPLE 5

Production of Folic Acid by Reacting Triaminopyrimidinone with (S)-2-[4-[3-[4-[(S)-1,3-Dicarboxy-propylcarbamoyl]-phenylimino]-2-hydroxy-propenylamino]-benzoylamino]-pentane-1,5-di-acid in Water 2.23 g (10 mmol) of triaminopyrimidinone sulphite, 1.26 g (10 mmol) of sodium sulphite and 30 ml of water are placed under nitrogen in a 100 ml 5-necked flask provided with a thermometer. Thereafter, 6.1 g of (S)-2-[4-[3-[4-[(S)-1,3-dicarboxy-propylcarbamoyl]-phenylimino]-2-hydroxy-propenylamino]-benzoylamino]-pentane-1,5-di-acid (diimine from Example 1) are slowly added at pH=6.0 and 38° C. while stirring. The pH value is held constant at pH=6.0 by dosing with 10 ml of 2M sodium carbonate solution. The reaction has finished after 6 hours. The folic acid in the red-brown mixture is determined as described in Example 1. HPLC analysis gives a folic acid yield of 64% of theory.

EXAMPLE 6

Production of 2-Hydroxymalondialdehyde by Acidic Hydrolysis of 2-Hydroxymalondialdehyde Tetraalkyl-acetal in the Presence of an Ion-exchanger A solution of 34,2 g (190 mml) 2-hydroxymalondialdehyde-tetraalkyl-acetal in 600 ml water is given to a glasstube (260×25 mm) at room temperature. The glasstube is filled with about 130 g DOWEX 50 W. The flow of the solution is 2.5 ml/minute.

The eluate is collected at about 0° C. under nitrogen and is concentrated to 50 g on a rotary evaporator at about 20 mbar. The suspension is lift at about 0° C. for 18 hours. The crude product is filtered off and is washed with 10 ml water. After drying under a water-jet vaccuum at 40° C. for 4 hours there are obtained 12.04 g 2-hydroxymalondialdehyde. M.p. 157°/8° C. under decomposition. Content of 98% (iodometric titration). From the filtrate there is additionally obtained 1.36 g 2-hydroxymalondialdehyde. Content 97% (iodometric titration).

Total yield: 13.4 g 2-hydroxymalondialdehyde=78% of theory.

I claim:

1. A process for the manufacture of folic acid derivatives of formula:

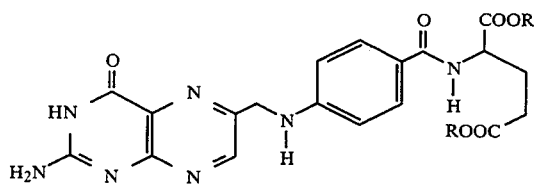

wherein R is hydrogen or lower alkyl, which comprises reacting a diimine of the formula:

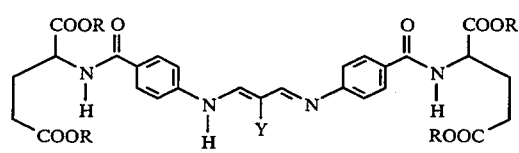

wherein R is as above and Y is hydroxy, halogen, phosphate, diphosphate, triphosphate or —COR' and R' is lower alkyl or phenyl, with triaminopyrimidinone in aqueous medium in the presence of a sulphite to form said folic acid derivatives.

2. The process of claim 1, wherein the pH of said aqueous medium is from about 3 to about 8.

3. The process of claim 1, wherein the temperature of said aqueous medium is from about 0° C. to about 100° C.

4. The process of claim 1, wherein said sulphite is formed in situ by the addition to the aqueous medium of inorganic compounds which form sulphites in water.

5. The process of claim 1, wherein said process is carried out in the presence of 0.3-3 mol equivalents of sodium sulphite to 1.0 mol equivalent of said diimine, the pH of said aqueous medium is from about 5 to about 7 and the temperature of said aqueous medium is from about 5° C. to about 40° C.

6. The process of claim 1, wherein said diimine is formed in situ in said aqueous medium by the addition to said aqueous medium a compound of formula:

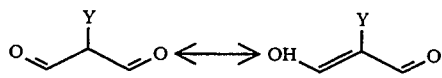

wherein Y is as in claim 1, with a compound of formula:

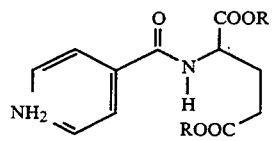

wherein R is as in claim 1, while said aqueous medium is under acidic conditions.

7. The process of claim 1, wherein said diimine is formed in situ in said aqueous medium by the addition to said aqueous medium a compound of formula:

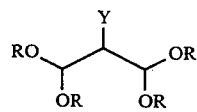

wherein R and Y are as in claim 1, with a compound of formula:

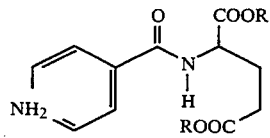

wherein R is as in claim 1, while said aqueous medium is under acid hydrolysis conditions.

8. A compound of formula:

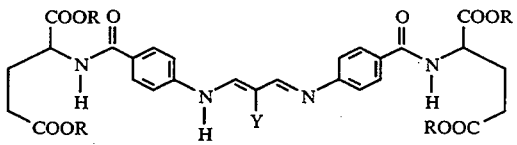

wherein R is hydrogen or lower alkyl and Y is hydroxy, halogen, phosphate, diphosphate, triphosphate or —O-COR' and R' is lower alkyl or phenyl.

9. The compound of claim 8, wherein R is hydrogen.

10. The compound (S)-2-[4-[3-[4-(S)-1,3-dicarboxy-propylcarbamoyl]phenylimino]-2-hydroxy-propenylamino]benzoylamino]-pentane- 1,5-di-acid.

* * * * *

UNITED STATES PATENT AND TRADEMARK OFFICE
CERTIFICATE OF CORRECTION

PATENT NO. : 5,410,056

DATED : April 25, 1995

INVENTOR(S) : Christof Wehril

It is certified that error appears in the above-indentified patent and that said Letters Patent is hereby corrected as shown below:

Column 7:

In claim 1, line 66, after the words triphosphate or -COR' should be

-- triphosphate or -OCOR' --

Signed and Sealed this

Twelfth Day of September, 1995

Attest:

BRUCE LEHMAN

*Attesting Officer*  *Commissioner of Patents and Trademarks*